United States Patent [19]

Patel et al.

[11] Patent Number: 4,726,945
[45] Date of Patent: Feb. 23, 1988

[54] HAIR RINSE CONDITIONER

[75] Inventors: Amrit Patel, Dayton; Harry Greenland, Martinsville, both of N.J.

[73] Assignee: Colgate-Palmolive Co., New York, N.Y.

[21] Appl. No.: 875,434

[22] Filed: Jun. 17, 1986

[51] Int. Cl.$^4$ .............................. A61K 7/06; A61K 7/08
[52] U.S. Cl. ....................................... 424/70; 514/938; 514/939
[58] Field of Search ................... 424/70; 514/938, 939

[56] References Cited

U.S. PATENT DOCUMENTS

| | | | |
|---|---|---|---|
| 4,144,326 | 3/1979 | Luediche, Jr. et al. | 424/70 |
| 4,149,551 | 4/1979 | Benjamin et al. | 424/70 |
| 4,160,823 | 7/1979 | Watanabe et al. | 424/70 |
| 4,183,917 | 1/1980 | Iwao et al. | 424/70 |
| 4,190,644 | 2/1980 | Green et al. | 424/70 |
| 4,206,195 | 6/1980 | Bolich, Jr. et al. | 424/70 |
| 4,206,196 | 6/1980 | Davis | 424/70 |
| 4,269,824 | 5/1981 | Villamarin | 424/70 |
| 4,423,032 | 12/1983 | Abe et al. | 424/70 |
| 4,436,722 | 3/1984 | Matsunaga et al. | 424/70 |
| 4,673,568 | 6/1987 | Grollier et al. | 424/70 |

FOREIGN PATENT DOCUMENTS 2102288  2/1983  United Kingdom ............... 424/70

*Primary Examiner*—Dale R. Ore
*Attorney, Agent, or Firm*—Richard N. Miller; Herbert S. Sylvester; Murray M. Grill

[57] ABSTRACT

A stable hair rinse composition which provides softness, shine, ease of combing, fly-away control (static control) and ease of styling and is easy to wash out with conventional anionic alkyl ether polyethenoxy sulfate-based shampoos without deposit or build-up consisting essentially of effective amounts of distearyl or ditallow quaternary ammonium compound, a $C_7$–$C_{17}$ alkylamido $C_2$–$C_3$ alkyl di-14 $C_1$–$C_2$ alkyl amine, propylene glycol, mineral oil, a $C_8$–$C_{18}$ alkanol and cyclomethicone in an aqueous vehicle.

8 Claims, No Drawings

HAIR RINSE CONDITIONER

FIELD OF INVENTION

The present invention relates to a novel hair rinse conditioner which provides softness, shine, manageability, fly-away control and ease of styling and is readily removable with conventional anionic alkyl ether polyethenoxy sulfate shampoos without build-up. The essential components of this composition are distearyl or ditallow quaternary ammonium compound, a $C_8$–$C_{18}$ alkanol, a $C_7$–$C_{17}$ alkylamido $C_2$–$C_3$ alkyl di-$C_2$–$C_3$ alkyl amine, mineral oil, cyclomethicone and propylene glycol in an aqueous medium.

BACKGROUND AND PRIOR ART

The absorption onto hair of quaternaries having long chain fatty portions as part of its molecule is the basis for most hair conditioner formulae. The fatty portion of the molecule which is largely attached to the substrate acts as a lubricant. The lubricating action makes combing easier.

It has been found that hair treated with a fatty quaternary or a conditioner containing a fatty quaternary and then washed with a conventional shampoo containing anionic alkyl ether polyethenoxy sulfate (AEPS) has a deposit on its surface. This deposit is a combination product formed by the interaction of the shampoo anionic surfactant with the quaternary of the conditioner. Thus, it is difficult to remove the cationic quaternary compound with conventional shampoos containing AEPS because of the formation of a cationic-anionic complex on the hair surface. Such deposit is not easily removed by conventional shampoo surfactants, and with continued use of the shampoo and the conditioner, the amount of this deposit or build-up tends to increase.

In the field of hair conditioning, the prior art is replete with hair conditioning compositions containing one or more of the components of the present novel and unique hair conditioner compositions. For example, U.S. Pat. No. 4,275,055 discloses compositions containing a stearamidopropyldimethylamine conditioning agent and U.S. Pat. Nos. 4,149,551 and No. 4,206,196 disclose conditioning articles having a di-higher alkyl dimethyl ammonium chloride or a fatty alcohol conditioning agent on a flexible substrate such as paper and the like. In U.S. Pat. Nos. 4,421,740 and 4,269,824, a composition is disclosed which employs the combination of di(hydrogenated tallow) dimethyl ammonium chloride and cetyl or stearyl alcohol. U.S. Pat. No. 4,436,722 discloses the combination of distearyl dimethyl ammonium chloride, cetyl alcohol and propylene glycol in hair conditioning compositions. U.S. Pat. Nos. 4,144,326 and 4,160,823 disclose similar compositions which include the combination of distearyl dimethyl ammonium chloride and propylene glycol; and U.S. Pat. No. 4,183,917 discloses a hair conditioner composition which comprises the combination of distearyl dimethyl ammonium chloride, mineral oil, cetyl alcohol and propylene glycol. However, U.S. Pat. Nos. 4,160,823; 4,436,722; 4,269,824 and 4,421,740 equate the mono-higher alkyl quaternary ammonium chloride with a di-higher alkyl quaternary ammonium chloride as the effective conditioning agent in their compositions and, therefore, teach away from the instant unique composition which is specific to the di-stearyl and di-tallow quaternary ammonium salts because it has been found that the substitution of a mono-higher alkyl quaternary compound for the di-higher alkyl compounds in the present composition adversely affects the conditioning properties thereof and the resultant conditioning agent is not completely removed by shampooing with AEPS shampoos, thereby creating a build-up of conditioner on the hair.

However, it is noted that none of the above cited patents discloses a hair conditioner composition comprising the mixture of a di-stearyl or di-tallow quaternary ammonium compound, a $C_8$–$C_{18}$ amido $C_2$–$C_3$ alkyl di-$C_1$–$C_2$ alkyl amine, a $C_{14}$–$C_{18}$ alcohol, mineral oil, cyclomethicone, and propylene glycol as the essential ingredients emulsified in an aqueous medium.

SUMMARY OF THE INVENTION

It has been found that a hair rinse conditioning composition comprising the mixture of di-stearyldi-$C_1$–$C_3$ alkyl ammonium compound, $C_7$–$C_{17}$ alkyl amido $C_2$–$C_3$ alkyl di-$C_1$–$C_2$ alkyl amine, a $C_{14}$–$C_{18}$ alkanol, mineral oil, cyclomethicone, and propylene glycol dispersed in an aqueous medium provides a stable composition having good conditioning properties, including good body, luster, combability, static control and ease of styling of the hair, which is readily rinseable without build-up.

Accordingly, a primary object of the present invention is to provide a hair rinse conditioner which imparts superior conditioning effects, softness and manageability, static control, and ease of combing.

Another object of present invention is to provide a hair rinse conditioning composition which is readily removable without build-up by conventional shampoos containing AEPS detergent.

Another object of the present invention is to provide a stable, non-irritating, rinse conditioner capable of being applied daily after shampooing.

Still another object of present invention is to provide a rinse conditioner which imparts a superior shine to the hair.

Another object of the present invention is to provide an economical hair rinse conditioner containing a minimum concentration of essential active ingredients.

Additional objects, advantages and novel features of the invention will be set forth in part in the description which follows, and in part will become apparent to those skilled in the art upon examination of the following specification or may be learned by practice of this invention.

To achieve the foregoing and other objects and in accordance with the present invention as embodied and broadly described herein, the novel hair conditioner composition of this invention consists essentially of about 0.5% to 2.5% by weight of a di-stearyl or di-hydrogenated tallow di-$C_1$–$C_3$ alkyl quaternary ammonium compound, about 0.5% to 2.0% by weight of $C_7$–$C_{17}$ alkylamido $C_2$–$C_3$ alkyl di-$C_1$–$C_2$ alkyl amine, about 1% to 10% by weight of a $C_{14}$–$C_{18}$ alkanol, about 0.2% to 1.5% by weight mineral oil, about 0.1% to 2% by weight of cyclomethicone and about 0.2% to 2% by weight propylene glycol in about 80% to 97.5% by weight of an aqueous carrier. The final product is in the form of an emulsion and has a pH of about 4–6 and preferably 4.5 to 5.5.

In a preferred aspect, the present invention relates to a stable hair conditioner composition which is easy to remove with a conventional shampoo containing AEPS detergent without undesirable build up on the hair and has a pH of about 4.5 to 5.5. consisting essentially of, by weight, about 0.7% to 2% of a quaternary ammonium compound selected from the group consisting of distearyl dimethyl quaternary ammonium chloride and di-hydrogenated tallow dimethyl quaternary ammonium chloride, about 0.75% to 1.5% of $C_{13}$–$C_{17}$ alkylamidopropyl dimethyl amine, about 1.5% to 4% of cetyl or stearyl alcohol, about 0.3% to 1.0% mineral oil, about 0.2% to 1% of cyclomethicone and about 0.4% to 1.5% of propylene glycol emulsified in 89% to 96.2% of water.

The described hair conditioner compositions are stable, opaque liquids at room temperature. Further, these compositions are stable at 5° C. and at 38° C. to 48° C. It is believed that these compositions are oil-in-water emulsions, with the two cationic compounds being the emulsifying agents.

As indicated, these compositions contain safe chemicals which are not irritating to the skin are non-toxic and are effective to improve the manageability of the hair.

It is believed that the good conditioning properties are imparted to the hair when the composition is applied to the hair with or without subsequent rinsing due to the use of the essential mixture of conditioning agents, namely di-stearyl or di-hydrogenated tallow, ammonium salt $C_7$–$C_{17}$ alkylamido $C_2$–$C_3$ alkyl amine, $C_{14}$–$C_{18}$ saturated alkanol and mineral oil. Additionally, it is believed that the co-action of the aforementioned essential ingredients is responsible for the ready removeability of this conditioning mixture in the course of normal shampooing with a conventional shampoo containing an AEPS detergent. Also, the conditioning mixture provides a balanced conditioning effect and better hair luster than is normally provided by the mixture of cationic conditioning compounds and said $C_{14}$–$C_{18}$ saturated alkanol. Furthermore, the mixture of cationic compounds serves as the emulsifier to yield the desired physical stability.

In addition, it has now been found that the present novel hair rinse conditioners are more readily and easily removed by shampooing with AEPS containing shampoo, resulting in negligible build-up of conditioner on the hair with extended use. A comparison with other formulae confirms that this is an unexpected and unusual property of the instant conditioners. It also has been found that this rinse conditioner leaves tresses shinier (cleaner) than when treated with other conditioners or with shampoos which usually contain anionic surfactants such as sodium lauryl ether sulfate (SLES), triethanolammonium lauryl sulfate (TEALS) and sodium lauryl sulfate.

DETAILED DESCRIPTION OF THE INVENTION

The long chain di-higher alkyl quaternary salts which are one of the essential compounds in the mixture of conditioning agents have been used in the prior art as hair conditioning agents. They are substantially water insoluble cationic surfactants, but stable aqueous dispersions thereof can be obtained in 4–8% concentrations. They are soluble in isopropanol, methanol and ethanol. Generally, these suitable cationic quaternary ammonium salts have the following formula:

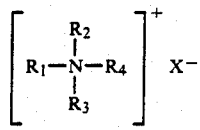

wherein $R_1$ and $R_2$ are stearyl groups, $R_3$ and $R_4$ are each alkyl groups of 1 to 3 carbon atoms and X is an anion selected from the group consisting of chloride, bromide and methyl sulfate. The term stearyl groups refers to the commercial distearyl quaternary ammonium compounds which contain about 95% by weight of stearyl alkyl groups as well as the commercially available di-hydrogenated tallow quaternary ammonium salts wherein the alkyl group is a mixtures of $C_{14}$–$C_{18}$ alkyl groups in which stearyl alkyl predominates. For eaxmple, the commercial quaternary salt sold under the tradename Arquad 2HT contains alkyl groups obtained by hydrogenation of the fatty acid derived from tallow which consists of 4% by weight of $C_{14}$ alkyl, 31% by weight of $C_{16}$ alkyl and 64% by weight of $C_{18}$ alkyl. Thus, the suitable di-stearyl quaternary ammonium compounds contain at least 60% by weight of stearyl alkyl groups. Representative examples of suitable distearyl quaternary ammonium salts include distearyl dimethyl ammonium chloride, di-hydrogenated tallow dimethyl ammonium chloride, distearyl diethyl ammonium bromide and distearyl dimethyl ammonium methyl sulfate.

The distearyl quaternary ammonium salts used in the present hair conditioning compositions may be obtained from a number of suppliers either in the form of a liquid or paste in an aqueous-isopropanol solvent at 25° C. or in the form of a solid. Prefered quaternary compounds are the (di-tallow) ammonium chloride purchased from Armak as a 74%–77% active paste in aqueous isopropanol containing 74–75% A.I. (active ingredient) under the tradename Arquad 2HT wherein the alkyl group is 4% $C_{14}$, 31% $C_{16}$ and 64% $C_{18}$ on a weight basis and the distearyl dimethyl ammonium chloride obtainable from the Sherex Chemical Co. in the form of a dry, free-flowing, white powder under the name Arosurf TA 100 wherein the alkyl is 2.5% $C_{16}$, 95% $C_{18}$ and 2.5% $C_{20}$ by weight. The distearyl di-$C_1$–$C_3$ alkyl ammonium salt is used in an amount of about 0.5% to 2.5%, preferably 0.7% to 2%, by weight of the composition.

The second component of the conditioning mixture employed in the hair conditioner compositions also is a cationic material, namely, $C_7$–$C_{17}$ alkyl amido $C_2$–$C_3$ alkyl di $C_1$–$C_2$ alkyl amine salt, which has been employed as a conditicningagent in prior art compositions. Examples of suitable cationic amines include stearamidopropyl dimethylamine, lauramidopropyl dimethylamine, cocoamidopropyl dimethyl amine, palmitamidopropyl dimethyl amine, myristamidoethyl dimethylamine and stearamidopropyl diethyl amine. (The foregoing list names the compounds based upon the alkanoic acid from which the amide is derived, e.g., stearamido is derived from the reaction of stearic acid and an organic amine, but the more proper nomenclature would be heptadecylamido because the amido group is a —C(O)N= radical.) Preferred amines are the $C_{13}$–$C_{17}$ alkyl amidopropyl dimethyl amines, with heptadecyl amidopropyl dimethyl amine being the most preferred. The proportion of said higher alkylamido lower alkyl di-lower alkyl amine in the final composition is about 0.5% to 2%, preferably 0.75% to 1.5%, by weight.

In the conditioner compositions, the $C_7$-$C_{17}$ alkylamido $C_2$-$C_3$ alkyl di $C_1$-$C_2$ alkyl amine compound is present in the form of an acid salt. Such salt is formed when the amine base is neutralized with a water-soluble acid to form the acidic cationic salt. Acids which are suitable for neutralizing the cationic amine include citric acid, acetic acid, lactic acid, tartaric acid, gluconic acid, hydrochloric acid and phosphoric acid, with citric acid being preferred. The amount of acid used should be sufficient to obtain a composition having a pH of 4–6 and preferably about 4.5 to 5.5.

In the conditioner product, the dialkyl quaternary salt and the alkyl amidoamine salt are the primary hair conditioning agents and are the emulsifiers. Additionally, the $C_7$-$C_{17}$ alkyl amido $C_2$-$C_3$ alkyl di-$C_1$-$C_2$ alkylamine salt is effective to modify the film of cationic material deposited on the hair so that the heavy coated feeling characteristic of the di higher alkyl quaternary salts is minimized. Thus, the proportions of the two cationic compounds are controlled in the range of 10:1 to 1:5, preferably 2:1 to 1:2 with respect to one another, said ratio being of dialkyl quaternary salt to alkyl amido amine salt.

The third compound in the mixture of conditioning agents is a $C_{14}$-$C_{18}$ alkanol. Since the preferred alkanols are obtained from fats and oils, these alkanols are often referred to as fatty alcohols. However, alkanols made by synthetic processes also are satisfactory. Examples of suitable alkanols are 1-tetradecanol, 1-hexadecanol, 1-heptadecanol, 1-octadecanol and mixtures of $C_{14}$-$C_{18}$ alkanols obtained by hydrogenating the fatty acids derived from tallow. Preferred higher alkanols are stearyl alcohol and cetyl alcohol. The proportion of $C_{14}$-$C_{18}$ alkanol present in the conditioner composition is about 1% to 10%, preferably 1.5% to 4%, by weight. Furthermore, the $C_{14}$-$C_{18}$ alkanol usually is the predominant compound in the mixture of conditioning agents because it is present in the largest percentage. Typically, the weight ratio of $C_{14}$-$C_{18}$ alkanol to the totalcationic surfactants ranges from about 2:1 to 0.75:1. It is believed that the $C_{14}$-$C_{18}$ alkanol functions as a co-emulsifying agent, thickens the emulsion and stabilizes the product.

The final essential compound in the mixture of hair conditioning agents is mineral oil—another compound employed in prior art hair conditioning products. Mineral oil is a homogeneous mixture of saturated aliphatic and alicyclic hydrocarbons derived from petroleum. Mineral oil is chemically and biologically inert and is hydrophobic in nature. Mineral oil is available in various viscosities. The proportion of mineral oil present in the hair rinse conditioner composition is about 0.2% to 1.5%, preferably 0.3% to 1.0%, by weight. Usually, the mineral oil represents less than 20% by weight of the mixtures of the four conditioning agents and preferably less than 10% by weight of said mixtures. Such controlled small amounts of mineral oil tend to counteract the dulling effects of the cationic surfactants by enhancing the shine of the hair and also function as a placticizer for the optional film forming polymers when they are present in the final composition. Further, the mineral oil assists in decreasing the amount of quaternary salt residue in the hair after shampooing.

The essential propylene glycol ingredient is a clear, viscous, colorless liquid which is hygroscopic and is completely miscible with water. Propylene glycol can penetrate the hair shaft and remain there after rinsing. The effect of this material is believed to result in a softening and swelling of the hair as well as providing a humectant effect, i.e., it enables the hair containing conditioners to retain its moisture and flexibility between shampooings. The amount of propylene glycol used in the final composition is about 0.2% to 2%, preferably 0.4% to 1.5%, by weight.

Another essential component is cyclomethicone which is a volatile cyclic silicone represented by the formula:

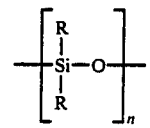

wherein R is a $C_1$-$C_3$ alkyl group or a phenyl group, preferably a methyl group; n is a number from 3 to 10, preferably 3 to 7, and the unsatisfied valencies on the oxygen and silicon atoms at the end of the chain are joined together to form a cyclic structure. Suitable cyclic silicones are available as low viscosity fluids from a number of manufacturers, including the General Electric Company. The most preferred cyclomethicones are decamethyl cyclopentasiloxane (General Electric's Silicone Fluid SF 1202) and octamethyl cyclotetrasiloxane (General Electric's Silicone Fluid SF 1173).

The cyclic silicones are non-polar, insoluble in water and completely miscible in lower alcohols, aliphatic aromatic solvents and halogenated hydrocarbon solvents. This ingredient facilitates the distribution of the mixture of conditioning agents on the hair and the quick spreading of the film of conditioners on the hair. The proportion of volatile cyclic silicone in the hair conditioner composition is about 0.1% to 2%, preferably 0.2% to 1.0%, by weight.

The final essential ingredient in the hair rinse conditioner composition is an aqueous medium which is primarily water. Since some of the di-stearyl di $C_1$-$C_3$ alkyl quaternary salts may be supplied in admixtures with a $C_2$-$C_3$ alcohol, e.g., isopropanol, the aqueous medium may contain a small amount of said $C_2$-$C_3$ alcohol. Furthermore, if desired, additional amounts of $C_2$-$C_3$ alkanol may be added to the composition, particularly where the composition is sold in the form of a "mousse." The proportion of the aqueous medium is in the range of 80% to 97.5%, preferably 89% to 96.2%, most preferably 90% to 95.0%, by weight of the hair rinse composition.

Optionally, the hair conditioner compositions may include a water-soluble nonionic, cellulose polymer as a thickening agent. Suitable cellulosic polymers are selected from the group consisting of hydroxyethyl cellulose and hydroxypropyl methyl cellulose, with hydroxyethyl cellulose being preferred. Hydroxyethyl cellulose is the product of reaction between an alkali cellulose and ethylene oxide, and such products are available in a number of viscosity grades. Viscosity is primarily dependent upon the viscosity of the cellulose used in the reaction. The degree of substitution of hydroxyethyl groups per glucose unit is 1.4–1.5, the hydroxyethyl molar substitution is 1.5–3.0 and these hydroxyethyl celluloses have an average molecular weight range from about 80,000 to about 900,000. A particularly preferred hydroxyethyl cellulose is available under the tradename Natrosol 250 HR from Hercules, Inc. Water-soluble hydroxypropyl methyl cellulose has a methoxyl content between about 25% and about 32% by weight and a hydroxypropyl content between about 2% to 10%, preferably 2% to 7%, by weight, Again, the chain length of the cellulose used in the reaction can be controlled to provide a molecular weight which yields a viscosity for a 2% solution in water in the range of 10 cps and 5000 cps, preferably 50 cps to 4000 cps.

These cellulose polymers provide stability to the composition upon aging by viscosity control. The composition retains its viscosity without thinning out or thickening. In addition to controlling the viscosity of the aqueous hair conditioner composition, the cellulose polymer tends to form a film on the hair having the mixture of conditioners thereon by hydrogen bonding with the cationic surfactants. When present, the proportion of nonionic cellulose polymer is about 0.25% to 2.5%, preferably 0.5% to 1.5%, by weight of the hair conditioner composition.

Another film forming polymer which may be included in the hair conditioner compositions in conjunction with the foregoing cellulose polymer is a water soluble, nonionic polyvinylpyrrolidone. Polyvinylpyrrolidone (PVP) is available in an average molecular weight range from about 10,000 to 360,000 and the type known commercially as PVP an average molecular weight of about 40,000 is preferred. K-30 having an average molecular weight of about 40,000 is preferred. Polyvinylpyrrolidone is available in the form of a powder (contains about 95% of polymer and 5% water) and in the form of an aqueous solution. It is believed that the polyvinylpyrrolidone cooperates with the cellulose polymer to form a clear film on the hair which assists in maintaining the shape of the hair, but also is smooth and pliable so that it does not interfere with combing. When present, the amount of polyvinylpyrrolidone is about 0.02% to 1%, preferably 0.05% to 0.5%, by weight of the final composition. Also, the polyvinylpyrrolidone usually is a minor amount of the mixture of polymers, i.e., about 4% to 15% by weight of the polymer mixture, so that a smooth, substantially non-tacky film is obtained. Amounts of polyvinylpyrrolidone in excess of 1% by weight yield a film which is too rigid and too tacky. The film formed by the coaction of the PVP with the nonionic cellulose polymer also is plasticized by the combination of propylene glycol and mineral oil.

The hair conditioner compositions of this invention also may contain conventional additional components such as coloring agents, perfumes, preservatives such as formaldehyde (formalin) and brighteners such as Uvinul. Other optional components are urea and d-glucose in amounts of 1-2% and 1-3% by weight respectively. The total weight of these optional additives usually does not exceed 5% by weight of the composition and preferably does not exceed 3% by weight of the composition, with the proportion of the individual ingredients often being 1% by weight or less.

The hair conditioner in accordance with the invention may be in the form of a pourable lotion or a smooth cream. Further, the final product may have any suitable viscosity so long as it is appropriate for the final form selected, e.g., a pourable lotion, a thick or viscous lotion or a cream.

The present hair conditioner compositions can be manufactured readily by simple mixing methods. For example, a preferred method of preparing the present compositions comprises the steps of dissolving the propylene glycol, the distearyl quaternary ammonium compound and an acid to adjust pH (citric acid) in the formula weight of water with agitation at a temperature of 40° C. to 90° C. to form a uniform aqueous solution; forming a separate mixture of the remaining water-insoluble ingredients, name $C_{14}$-$C_{18}$ alkanol, $C_7$-$C_{17}$ alkylamido $C_2$-$C_3$ alkyl di-$C_1$-$C_2$ alkyl amine, mineral oil and cyclomethicone and heating said mixture to a temperature of about 70° C. to 85° C.; adding the mixture of water-insoluble ingredients to the aqueous mixture with slow agitation while maintaining the temperature in the range of 80° C. to 85° C.; cooling the resultant emulsion to 35° C. to 45° C. with slow agitation; adding any optional ingredients to the foregoing mixture; and cooling the resultant composition to 25° C. to 30° C. in the presence of slow agitation to form a stable, opaque emulsion having a pH in the range of 4 to 6. Any required adjustment of pH usually is made during the cooling step by adding an appropriate concentration of acid or alkali metal hydroxide.

When polymers are present, the cellulose polymer usually is dispersed in water at a temperature of 80° C. to 85° C. prior to the sequential addition of propylene glycol, di-stearyl quaternary salt and acid ingredient and the polyvinylpyrrolidone polymer is dissolved in water and added to the product during the cooling step at 35° C. to 45° C.

The following examples merely illustrate the invention, but it is understood that the invention is not limited thereto. All amounts of various ingredients in the examples and elsewhere in the specification are by weight unless otherwise specified.

EXAMPLES 1-4

Examples 1 and 2 describe preferred compositions and Examples 3 and 4 are comparatives containing other di-higher alkyl quaternary ammonium salts.

EXAMPLES 1-4

Hair Conditioner

| | Hair Conditioner | | | |
|---|---|---|---|---|
| | 1 | 2 | 3 | 4 |
| Stearyl Alcohol | 2.50 | 2.50 | 2.50 | 2.50 |
| Stearamidopropyl Dimethylamine | 1.00 | 1.00 | 1.00 | 1.00 |
| Mineral Oil | 0.50 | 0.50 | 0.50 | 0.50 |
| Cyclomethicone(a) | 0.25 | 0.25 | 0.25 | 0.25 |
| Propylene Glycol | 0.50 | 0.50 | 0.50 | 0.50 |
| Deionized Water | 92.90 | 92.65 | 92.17 | 92.15 |
| Hydroxyethylcellulose(b) | 1.00 | 1.00 | 1.00 | 1.00 |
| Citric Acid | 0.20 | 0.20 | 0.20 | 0.20 |
| Polyvinylpyrrolidone(c) | 0.10 | 0.10 | 0.10 | 0.10 |
| Perfume | 0.20 | 0.20 | 0.20 | 0.20 |
| Formalin | 0.10 | 0.10 | 0.10 | 0.10 |
| Dicetyl Dimonium Chloride(d) | — | — | 1.48 | — |
| Distearyl Dimonium Chloride(e) | 0.75 | — | — | — |
| Di(hydrogenated tallow)(f) Dimonium Chloride | — | 1.00 | — | — |

| -continued | | | | |
|---|---|---|---|---|
| | Hair Conditioner | | | |
| | 1 | 2 | 3 | 4 |
| Dilauryl Dimonium Chloride[g] | — | — | — | 1.50 |

[a] Purchased from General Electric as Silicone Fluid SF 1202
[b] Purchased from Hercules as Natrosol 250H
[c] Purchased from GAF Corporation as PVP K-30
[d] Purchased from Sherex Chemical as Adogen 432 CG which contains 74% by weight of ($C_{12}$-$C_{18}$) dialkyl ammonium chloride having the following alkyl distribution by weight: $C_{12}$-16%, $C_{13}$-23%, $C_{14}$-13%, $C_{15}$-9%, $C_{16}$-24%, $C_{18}$-14%, $C_{20}$-1%
[e] Purchased from Sherex Chemical under the name Arosurf TA-100
[f] Purchased from Armak as a 75% dispersion in aqueous isopropanol under the name Arquad 2HT (The alkyl distribution by weight is 4% $C_{14}$, 31% $C_{16}$ and 64% $C_{18}$.)
[g] Purchased from Humko under the name of Kemamine Q-6902 C as a 75% dispersion of dialkyl quaternary salt having an alkyl distribution by weight of 5% $C_{10}$, 90% $C_{12}$ and 5% $C_{14}$.

In preparing the hair conditioners of Examples 1–4, the hydroxyethylcellulose is dispersed in deionized water and mixed until a uniform clear solution is obtained and heated to 80°–82° C. with mixing. The propylene glycol, the long chain alkyl quaternary chloride and citric acid are added to and mixed with the aqueous hydroxyethyl cellulose solution at 80°–82° C. until a uniform aqueous solution is obtained. The stearyl alcohol, stearamidopropyl dimethylamine, mineral oil and cyclomethicone are slowly mixed and heated at 80°–82° C. in a small mixer until a uniform clear solution is obtained which is slowly added to, and mixed with the aqueous solution at 80°–82° C. After addition is completed, the emulsion mixture is mixed for another 20 minutes and slowly cooled at 38°–40° C. Polyvinylpyrrolidone dissolved in 1% deionized water is added to the emulsion at 38°–40° C. with mixing and mixing is continued while the composition is cooled to 25°–30° C. The perfume and formalin are added to the emulsion at 25°–30° C. with mixing. The final products are white smooth pourable lotions which are stable under all conditions of aging.

The wet combing properties and the sodium lauryl ether triethenoxy sulfate-based shampoo removeability of the hair conditioning rinse compositions of Examples 1–4 is set forth in Table I below. In the evaluation reported in Table I, prewashed hair tresses of virgin European hair 8 inches to 10 inches in length are wetted with water, treated with the test hair conditioner composition, rinsed and combed and thereafter treated with an aqueous shampoo containing 10% by weight of sodium lauryl ether diethenoxy sulfate, rinsed and combed. This treatment is repeated three times and 6 times to illustrate the effects of multiple hair treatments. All hair tresses are prewashed with the aqueous sodium lauryl ether sulfate shampoo for one minute, rinsed under flowing tap water at 40° C. for one minute and dried. In the test procedure, each hair tress is wetted with 40° C. water, squeezed dry and treated with one gram of the test conditioner composition which is worked into the tress for one minute using the fingers. Thereafter, the tress is rinsed under flowing 40° C. water for one minute and combed by a combing expert to indicate the wet combing properties of the hair conditioner. Then the conditioned tress is shampooed with one gram of said sodium lauryl ether diethenoxy sulfate shampoo for one minute by thoroughly working the shampoo into the tress for one minute with the fingers so as to generate a foam. The shampooed tress is rinsed with flowing water at 40° C. for one minute and the tress is combed to define the wet combing properties of the shampooed tress in order to indicate the degree of removal of the test conditioner by said shampoo. The same tresses are alternatively treated three or six times with conditioner and said shampoo, ending with the shampoo, to simulate what happens upon continued usage of conditioner. As indicated above, combability tests are done by six combing experts and combability is rated on a scale of one to five based upon the degree of work to pass the comb through the tress. Hair treated with only a conditioning agent (hair conditioner control) is rated five and hair subject to shampooing only (shampoo control)—no conditioner—is rated one in terms of wet combability. All of the tabulated results in Table I are based upon the average of six readings.

TABLE I

| Composition | Wet Combability Results | | | | |
|---|---|---|---|---|---|
| | First Condit. | First Shampoo | Three Shampoos | Six Condit. | Six Shampoos |
| Ex. 1 | 5.50 | 0.72 | 0.67 | 5.14 | 1.00 |
| Ex. 2 | 4.00 | 0.86 | 0.62 | 5.70 | 0.75 |
| Ex. 3 | 6.60 | 1.22 | 1.21 | 6.57 | 1.78 |
| Ex. 4 | 5.38 | — | 2.15 | 5.05 | 2.90 |
| Shampoo Control | 1.10 | 1.00 | 0.67 | 1.00 | 0.71 |
| Hair Conditioner Control | 4.66 | 1.93 | 2.04 | 5.00 | 1.50 |

The results in Table I indicate that essentially no build-up of conditioner on hair surfaces is found after extended use (six shampoos) with the compositions of the instant invention (Examples 1 and 2). As a matter of fact, the hair treated with the inventive conditioner is cleaner than the control after one and three shampooings. These results also show specificity of the use of the di-stearyl alkyl (distearyl or hydrogenated ditallow) quaternary compounds in the present unique readily rinseable hair conditioner. More specifically, each of the dicetyl and dilauryl quaternary ammonium salt containing compositions shows a build up of conditioner on the treated hair after shampooings (Examples 3 and 4).

EXAMPLE 5

The importance of employing the di-stearyl quaternary ammonium salt as the primary conditioning agent in the inventive compositions is apparent from Table II below which sets forth wet combability results for hair tresses treated first with one gram of the composition of example containing 0.75% by weight of the various quaternary conditioning agents, rinsed for one minute with flowing water at 40° C. and evaluated for wet combability followed by shampooing of the conditioned tress for one minute with a sodium lauryl ether diethenoxy sulfate shampoo (10% of organic sulfate), rinsing of the shampooed tress for one minute with 40° C. flowing water and the evaluation of the shampooed and rinsed tress for wet combability.

TABLE II

| | Wet Combability Results | | | | | | |
|---|---|---|---|---|---|---|---|
| | Cetyl Trimethyl Ammonium Chloride | Stearyl Trimethyl Ammonium Chloride | Tallow Trimethyl Ammonium Chloride | Lauryl Trimethyl Ammonium Chloride | Distearyl Dimethyl Ammonium Chloride | Ditallow Dimethyl Ammonium Chloride[f] | Shampoo Control |
| Conditioned[a] | 2.36 | 3.93 | 3.43 | 3.25 | 4.10 | 4.45 | — |
| Shampooed[a] | 0.81 | 0.81 | 0.84 | 0.85 | 0.39 | 0.46 | 0.67 |

[a]Third cycle of alternating conditioner-shampoo treatments

These results show that the cetyl, stearyl, tallow, and lauryl trimethyl ammonium chlorides are not as good as di-hydrogenated tallow and distearyl dimethyl ammonium chlorides for effecting high conditioning as measured by wet combability. Furthermore, Table II shows that the mono-$C_{12}$–$C_{18}$ alkyl quaternary builds up to a greater extent after three treatment cycles than the distearyl quaternary salts despite the fact that a greater deposition of the distearyl compounds occurs in each conditioner treatment.

In addition, the 0.67 value for the shampoo control suggests that the tresses treated with the distearyl quaternary compounds are cleaner than the control because the wet combability values of 0.39 and 0.46 indicate less residue on the treated tresses than on the shampoo control.

The lower build-up of conditioner on the conditioned hair after multiple use also is confirmed by Electrospectrochemical (ESCA) measurements on individual hairs from tresses treated with various hair conditioning compounds. As in Examples 1–5, prewashed hair tresses are treated with the test conditioner composition, rinsed, shampooed with sodium lauryl ether diethenoxy sulfate and rinsed six times prior to being dried and examined using an electrospectrochemical analyzer. In such analysis, the deposition of both cationic conditioner and anionic sodium lauryl ether diethenoxy sulfate is determined by the relative percentages of two chemical forms of nitrogen and sulfur observed at the surface of the various hair samples. More specifically, sulfur exists in two chemical forms at the hair surface, namely $S^{II}$ and $S^{VI}$, while the anionic sulfate contains only $S^{VI}$. Thus, the deposition of anionic sulfate at the hair surface is indicated by an increase in $S^{VI}$ content as compared to $S^{II}$. Similarly, nitrogen exists in quaternary and non-quaternary form. The results of ESCA studies on tresses treated with various conditioner test-shampoo treatments (six alternating treatments of the listed conditioner followed by shampooing with sodium lauryl ether diethenoxy sulfate) are shown in Table III below.

TABLE III

| Conditioner | Relative % of N(Quat) | Relative % of N(Hair) | $S^{II}$ | $S^{VI}$ | Atomic % of N |
|---|---|---|---|---|---|
| A. None (shampoo only | — | 100 | 69 | 31 | 6.5 |
| B. Distearyl Dimonium Chloride + Urea* | — | 100 | 69 | 31 | 7.1 |
| C. Distearyl Dimonium Chloride | — | 100 | 72 | 28 | 8.2 |
| D. Ditallow Dimonium Chloride | — | 100 | 74 | 26 | 7.2 |
| E. Dicetyl Dimonium Chloride[d] + Urea** | 6 | 94 | 61 | 39 | 7.5 |
| F. Dicetyl Dimonium Chloride[d] + Glucose*** | 10 | 90 | 62 | 38 | 6.4 |

*Example 1 composition with 0.75% by weight of the named di-alkyl quat and 2.0% by weight of urea
**Example 1 composition with 0.75% by weight of the named dialkyl quat and 2.0% by weight of urea
***Example 1 composition with 0.75% of the named dialkyl quat and 2.0% by weight of d-glucose.

Table III indicates that ESCA analysis shows deposition of only dicetyl dimonium chloride (samples E and F), with such deposition being in the form of an anionic cationic complex based upon the increase in $S^{VI}$ relative to $S^{II}$. Thus, the ESCA studies show that the build up of non-distearyl quaternary ammonium conditioners on the hair that is not removed by shampooing with a shampoo containing an anionic alkyl ether polyethenoxy sulfate surfactant is in the form of an anionic-cationic complex.

EXAMPLE 6

The criticality of all of the six essential components in the present novel rinse conditioning composition is illustrated by the wet combability tests in Table IV, for compositions corresponding to the composition of Example 1 wherein one or more of the essential components are excluded from the composition. The results in Table IV are based upon the same evaluation test employed in the prior examples, with the values for one conditioner cycle and one and three conditioner-shampooing cycles being set forth.

TABLE IV

| | WET COMBABILITY RESULTS FORMULA MODIFICATION | | | | | | | | |
|---|---|---|---|---|---|---|---|---|---|
| Treatment | 1 Ex. 1 | 2 No Propylene Glycol | 3 No Cyclomethicone | 4 No Mineral Oil | 5 No Amido Amine | 6 No Distearyl Quat | 7 Only Distearyl Quat, Stearyl Alcohol & Water | 8 No Cyclomethicone, no amido amine | 9 Shampoo Control |
| One conditioner application | 5.6 | 4.75 | 4.85 | 4.95 | 3.31 | 2.22 | 2.55 | 3.0 | 1.30 |

TABLE IV-continued

WET COMBABILITY RESULTS
FORMULA MODIFICATION

| Treatment | 1 Ex. 1 | 2 No Propylene Glycol | 3 No Cyclomethicone | 4 No Mineral Oil | 5 No Amido Amine | 6 No Distearyl Quat | 7 Only Distearyl Quat, Stearyl Alcohol & Water | 8 No Cyclomethicone, no amido amine | 9 Shampoo Control |
|---|---|---|---|---|---|---|---|---|---|
| One conditioner-one shampooing | 1.08 | 1.65 | 1.39 | 1.91 | 1.33 | 0.46 | 1.57 | 2.0 | 1.16 |
| Three conditioner-three shampooings | 1.0 | 2.29 | 2.20 | 1.66 | 1.96 | 0.66 | 1.62 | 1.83 | 0.75 |

Compositions 1 and 6 show that the distearyl quaternary salt is the principal conditioning agent and that conditioner build up is not a problem if it is omitted from the conditioner composition. Compositions 1–8 show that all of the essential components contribute to the conditioning effect as well as to the removeability shampoo containing alkyl ether polyethenoxy sulfate. (Said sulfate is a primary detergent in many of the principal commercial shampoos.) Compositions 5 and 8 indicate that the alkylamido amine also is an important conditioner. Compositions 2 and 3 indicate that each of propylene glycol and cyclomethicone are needed to facilitate removal of the conditioner by said shampoo, but Composition 1 makes it clear that all of the essential components are essential to obtain both the good conditioning and read removeability of the conditioners with the specified shampoo.

Other satisfactory conditioner compositions are set forth in Examples 7–10 below.

EXAMPLES 7 and 8

| Ingredients | % by weight | |
|---|---|---|
| | 7 | 8 |
| Cetyl Alcohol | 2.00 | 2.00 |
| Stearamidopropyl Dimethylamine | 1.00 | 1.00 |
| Mineral Oil | 0.25 | 0.25 |
| Cyclomethicone | 0.25 | 0.25 |
| Propylene Glycol | 0.25 | 0.25 |
| Hydroxyethylcellulose | 1.00 | 1.00 |
| Citric Acid | 0.20 | 0.20 |
| Polyvinylpyrrolidone | 0.10 | 0.10 |
| Perfume | 0.20 | 0.10 |
| Formalin | 0.10 | 0.10 |
| Distearyl Dimonium Chloride (Arosurf TA-100)(e) | 0.75 | — |
| Di-(hydrogenated tallow) Dimonium Chloride (Arquad 2HT-75)(f) | — | 1.00 |
| Deizonized Water | 93.90 | 93.75 |

The composition of Examples 7 and 8 are low cost formulations and contain a lower level of solids (active ingredients), but are effective hair rinse conditioners as shown by the wet combing tests in Table V.

TABLE V

| Shampoo only | Wet Combing Test Example | | Commercial Conditioner A* |
|---|---|---|---|
| | 7 | 8 | |
| 1.0 | 6.16 | 6.16 | 5.00 |

*Commercial conditioner A contains 1% by weight of $C_{20}$-$C_{22}$ alkyl trimethyl ammonium chloride as the principal conditioning agent.

The preceding results are the average of six readings. The results are obtained after one cycle which comprises rinsing a prewahsed hair tress, a conditioner treatment and rinsing. The tabulated values exceed the maximum raing of 5 on the 1–5 scale because the evaluators felt that the experimental formulas were superior to the product which was considered to give a 5 in wet combability.

EXAMPLES 9 and 10

| Ingredients | % by weight | |
|---|---|---|
| | Example 9 | Example 10 |
| Stearyl alcohol | 2.5 | 2.5 |
| Stearamidopropyl dimethylamine | 1.0 | 1.0 |
| Mineral oil | 0.5 | 0.5 |
| Cyclomethicone | 0.25 | 0.25 |
| Propylene glycol | 0.5 | 0.5 |
| Citric Acid | 0.2 | 0.2 |
| Perfume | 0.2 | 0.2 |
| Formalin | 0.1 | 0.1 |
| Distearyl dimethyl ammonium chloride | 0.75 | — |
| Ditallow dimethyl ammonium chloride | — | 1.0 |
| Deionized water | Q.S. | Q.S. |
| Total | 100.0 | 100.0 |

Tresses treated with the compositions of Examples 1 and 9 were mounted on an apparatus designed for visual assessment of shine for comparison with tresses treated with commercial hair conditioner products and with a tress which was shampooed with a shampoo containing 10% by weight of sodium lauryl ether diethenoxy sulfate. Commerical Conditioner A contained 1% by weight of $C_{20}$-$C_{22}$ alkyl trimethyl ammonium chloride as the conditioning agent; commercial Conditioner B contained 2% by weight of dicetyl dimethyl ammonium chloride as the conditioning agent; and commercial Conditioner C contained 1.5% by weight of 1.5% of quaternium-22 (gluconamidopropyl dimethyl-2-hydroxyethyl ammonium chloride) and 4.5% of quaternium-21 (PPG 40 diethylammonium chloride) as the conditioning agent. As in the prior described tests, prewashed tresses were wetted with water, thoroughly contacted with one gram of test conditioner for one minute, rinsed with flowing 40° C. water for one minute, squeezed dry and dried before mounting on the apparatus. The tresses were rated by twenty persons and the tresses treated with the compositions of Examples 1 and 9 received the highest ratings and were preferred for shine.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A stable hair rinse conditioner composition which is readily washed out of the hair by conventional shampoos containing an anionic alkyl ether polyethenoxy sulfate detergent consisting essentially of about 0.5% to 2.5% by weight of a di-stearyl or di-hydrogenated tallow quaternary di-$C_1$-$C_3$ alkyl ammonium compound; about 0.5% to 2.0% by weight of $C_7$-$C_{17}$ alkylamido $C_2$-$C_3$ alkyl di-$C_1$-$C_2$ alkyl amine; about 1% to 10% by weight of a $C_{14}$-$C_{18}$ alkanol; about 0.2% to 1.5% by weight mineral oil; about 0.1% to 2% by weight of a cyclic silicone of the formula

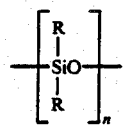

wherein R is a $C_1$-$C_3$ alkyl group or phenyl group and n is a number from 3 to 10; and about 0.2% to 2% by weight of propylene glycol in 80% to 97.5% by weight of an aqueous carrier, said composition being in the form of an emulsion.

2. A composition according to claim 1 wherein said quaternary ammonium compound is distearyl dimethyl ammonium chloride.

3. A composition according to claim 2 wherein said quaternary ammonium compound is di-$C_{14}$-$C_{18}$ alkyl dimethyl ammonium chloride wherein said alkyl portion is derived from the hydrogenation of tallow and contains at least 60% by weight of stearyl alkyl groups.

4. A composition according to claim 1 wherein said amine is a $C_{13}$-$C_{17}$ alkyl amidopropyl dimethyl amine.

5. A composition according to claim 1 wherein said composition has a pH of about 4 to 6.

6. A composition according to claim 1 wherein said di-higher alkyl quaternary compound is present in an amount of 0.7% to 2.0% by weight; said alkyl amine is a $C_{13}$-$C_{17}$ alkyl amidopropyl dimethyl amine and is present in an amount of 0.75% to 1.5% by weight; said alkanol is stearyl alcohol or cetyl alcohol and is present in an amount of 1.5% to 4% by weight; said mineral oil is present in an amount of 0.3% to 1% by weight; said cyclic silicone is a dimethyl silicone wherein n is 3 to 7 and is present in an amount of 0.2% to 1% by weight; said propylene glycol is present in an amount of 0.4% to 1.5% by weight, said aqueous carrier is water and is present in an amount of 89% to 96.2% by weight; said composition having a pH of 4.5 to 5.5.

7. A composition according to claim 6 wherein said quaternary ammonium compound is distearyl dimethyl ammonium chloride.

8. A composition according to claim 6 wherein said quaternary ammonium compound is di-$C_{12}$-$C_{18}$ alkyl dimethyl ammonium chloride, wherein said alkyl portion is derived from hydrogenation of tallow and contains at least 60% by weight of stearyl alkyl groups.

* * * * *